US 6,451,611 B1

(12) United States Patent
Simonsen et al.

(10) Patent No.: US 6,451,611 B1
(45) Date of Patent: Sep. 17, 2002

(54) QUANTITATIVE ANALYSIS OF HEXOSE-MONOPHOSPHATES FROM BIOLOGICAL SAMPLES

(75) Inventors: Henrik Simonsen, Rungsted Kyst; Ulrich Glümer Jensen, Taastrup; Niels Jacob Brandt, Holte; Ernst Christensen, Frederiksberg, all of (DK)

(73) Assignee: Statens Serum Institute, Copenhagen (DK)

( * ) Notice: Subject to any disclaimer, the term of this patent is extended or adjusted under 35 U.S.C. 154(b) by 0 days.

(21) Appl. No.: 09/627,978

(22) Filed: Jul. 28, 2000

(51) Int. Cl.[7] ............................................... G01N 33/00
(52) U.S. Cl. .................... 436/94; 436/103; 436/104; 436/811; 436/173; 435/14; 435/72; 435/105
(58) Field of Search .................... 436/94, 103, 104, 436/173, 811; 435/14, 72, 105

(56) References Cited

U.S. PATENT DOCUMENTS 5,352,590 A * 10/1994 Kato et al. ................... 435/105
5,439,803 A * 8/1995 Ross et al. ..................... 435/15

OTHER PUBLICATIONS

Slater "spectrophotometric determination of fructose 1,6–diphosphate, hexose monophosphate, adenosine triphosphate, and adenosine diphosphate", Biochem. J., 1953, v. 53, pp. 157–167, Abstract (STN search, L12, Answer 3).*
Ahlbehrendt et al. "Screening for galactose 1–phosphate urildylytransferase deficiencies (classic galactosemia) in newborns", Acta Biol. Med. Ger., 1977, v. 36, No. 5–6, pp. 797–800 (STN search,L63, Answer 6).*
Katz et al. "Application of mass isotopomer analysis for determination of pathways of glycogen synthesis", Am. J. Physiology, 1991, v. 261, 3 Pt. 1, E332–6, Abstract (STN Search, L84, Answer 6).*
Smits et al. "Cleanup and analysis of sugar phosphates in biological extracts by using solid–phase extraction and anion–exchange chromatography with pulsed amperometric detection", Anal. Biochem., 1998, v. 261, No. 1, pp. 36–42, Abstract (STN Search, L50.*
Mitchell et al. "Gas chromatographic–mass spectrometric analysis of hexose monophosphate shunt activity in cultured cells", Biochem. Biophys. Res. Comm., 1989, vol. 158, No. 2, pp. 474–479.*
Dahlqvist "A fluorometric method for the assay of galactose–1–phosphate in red blood cells", J.Lab. Clin. Med., 1971, v. 78, No. 6, pp. 931–938, Abstract (STN Search, L84, Answer 22).*
Xu et al. "HPLC analysis of uridine diphosphate sugars: decreased concentrations of uridine diphosphate galactose in erythrocytes and cultured skin fibrolasts from classical galactosemia patients", Clin. Chem. Acta, 1995, v. 240, No. 1, pp. 21–33, Abstract.*
Beutler E and Baluda MC. A simple spot screening test for galactosemia. J Lab Clin Med 1966;84:331–335.
Fujimoto A, Okano Y , Miyagi T , Isshiki G, Oura T. Clin Chem 2000;46:806–10.

(List continued on next page.)

*Primary Examiner*—Jill Warden
*Assistant Examiner*—Yelena Gakh
(74) *Attorney, Agent, or Firm*—Drinker Biddle & Reath LLP (57) ABSTRACT

The invention is for a method of quantitatively analysing the hexose monophosphate (HMP) composition of a biological sample, preferably a dried blood sample, using tandem mass spectrometry and for a method for quantitatively analysing the abundance of amino acids acylcarnitines and HMP from the same biological sample (such as a dried blood spot sample). The method is useful in screening infants for galactosemia and can be integrated with a method of screening for disorders in the metabolism of amino acids, organic acids and fatty acids.

41 Claims, 5 Drawing Sheets

OTHER PUBLICATIONS

Fujimura Y, Ishii S, Kawamura M, Naruse H. Microdetermination og galactose and galactose–1– phosphate in dried blood spots. Anal Biochem 1981;117:187–95.

Hill G, O'Reilly D, Robertson E. A simple screening test for galactosemia based on accumulation of galactose and galactose–1–phosphate. In: Naruse H, Irie M (eds.). Proceedings International Symposium on Neonatal Screening for Inborn Errors of Metabolism. Amsterdam: Excerpta Medica 1983;252–3.

Komrower GM. Galactosemia—Thirty years on. The experience of a generation. J Inher Metab Dis 1982;5 Suppl 2:96–104.

Naylor EW, Chace DH. Automated tandem mass spectrometry for mass newborn screening for disorders in fatty acid, organic acid, and amino acid metabolism. J Child Neurol 1999;14 Suppl 1:S4–8.

Nørgaard–Pedersen B, Simonsen H. Biological specimen banks in neonatal screening. Acta Paediatr Suppl 1999;88(432):106–9.

Paigen K, Pacholec F, Levy HL. A new method of screening for inherited disorders of galactose metabolism. J Lab Clin Med 1982;99:895–907.

Pollitt RJ, Green A, McCabe IJ, Booth A, Cooper NJ, Leonard JV et al. Neonatal screening for inborn errors of metabolism: cost, yield and outcome. Health technology assessment 1997;1:49–51.

Rashed MS, Bucknall MP, Little D, Awad A, Jacob M, Alamoudi M, et al. Screening blood spots for inborn errors of metabolism by electrospray tandem mass spectrometry with a microplate batch process and a computer algorithm for automated flagging of abnormal profiles. Clin Chem 1997;43:71129–1141.

Schweitzer S. Newborn mass screening for galactosemia. Eur J Pediatr 1995;154, suppl 2:S37–S39.

Segal S, Berry GT. In: Scriver CR, Beaudet AL, Sly WS, Valle D. The Metabolic and Molecular Bases of Inherited Disease. 7. ed. 1995;1:967–1000.

Waggoner DD, Buist NR, Donnel GN. Long–term prognosis in galactosemia: results of a survey of 350 cases. J Inherit Metab Dis 1990;13:802–818.

Walter JH, Collins JE and Leonard JV. Recommendations for the management of galactosemia. Arch Dis Child 1999;80:93–96.

Wolucka BA, Rush JS, Waechter CJ, Shibaev VN and Hoffmann E. An electrospray–ionization tandem mass spectrometry method for determination of the anomeric configuration of glycosyl 1–phosphate derivatives. Analytical Biochemistry 1998;255–251.

* cited by examiner

QUANTITATIVE ANALYSIS OF HEXOSE-MONOPHOSPHATES FROM BIOLOGICAL SAMPLES

FIELD OF THE INVENTION

The invention relates to a method of detecting hexose-monophosphates (HMPs) in biological samples and uses therefor. In a preferred embodiment, the method of the invention can be used to screen newborns for galactosemia.

BACKGROUND OF THE INVENTION

Galactosemia is a life-threatening disorder with severe symptoms in the neonatal period. It is caused by deficiency of the enzyme galactose-1-phosphate uridyl transferase (GALT) (EC. 2.7.7.12), (OMIM 230400).

In this disorder ingestion of milk causes accumulation of galactose in blood and urine and leads to a high intracellular concentration of galactose-1-phosphate (Gal-1-P). Gal-1-P is considered toxic for several tissues, especially the liver, brain, and renal tubules (12). The main symptoms appear shortly after ingestion of milk and include vomiting, failure to thrive, jaundice due to liver damage, and lethargy. The patients become comatose, and if treatment is not initiated early, death often occurs during the first weeks of life. Treatment with a galactose-free diet causes regression of symptoms and signs within a week or two. However, due to the low frequency of the disease (approximately 1:35000 in Denmark) and sub-optimal clinical awareness, diagnosis is often delayed or symptoms are misinterpreted as septicemia or isoimmunization, causing sequelae due to late intervention. While these considerations seem to advocate neonatal screening, this is still controversial as illustrated by two recent comprehensive reviews with opposing conclusions (11, 9). There are no controversies over the serious implications of untreated galactosemia: neonatal death or severe mental retardation. The major issues in the discussion are the low frequency of the disease affecting the cost benefit ratio, sub-optimal screening tests, and sequelae in the long-term outcome despite early diagnosis and treatment, such as intellectual impairment, speech disorders, cataracts, and hypergonadotrophic hypogonadism (13, 14, 5).

Several methods exist for neonatal screening for galactosemia. The simplest of all is examining the urine for reducing substances (i.e, using Fehling's and Benedict's solution). The commonly employed tests for neonatal screening use dried blood spot samples (DBSS). Paigen's (8) quantifies galactose and Gal-1-P by a microbiological assay. However, it is not suitable for automation, is sensitive to antibiotic otic treatment of the newborns or their mothers, and careful bacterial maintenance procedures are required. Measurement of GALT activity is the basis of the Beutler test (1, 2). GALT is sensitive to inactivation by heat or humidity, causing false-positive screening results. The Paigen and Beutler assays in combination are used by many screening laboratories (11) and can detect deficiencies in GALT, galactokinase, and galactose epimerase, but have relatively high false-positive rates (11). These disorders can also be detected by the alkaline phosphatase-galactose dehydrogenase assay (3, 4).

There is a need for an improved, more accurate, rapid, cost effective and easier method for screening for and diagnosing galactosemia.

SUMMARY OF THE INVENTION

The present inventors have developed a simple, fully automated, rapid and cost effective screening method to detect and quantify Hexosemonophosphates (HMPs). The method can be used to detect and quantify HMP in a biological sample. As such the method can be used as an indicator e.g. to diagnose screen for or identify patients at risk, for a disorder related to abnormal HMP levels (either relative or absolute). Such disorders include, but are not necessarily limited to: galactosemia, fructosuria, hereditary fructose intolerance, fructose 1,6, biphosphatase deficiency, glucose-6-phosphate dehydrogenase deficiency and diabetes meritus. In a preferred application, the method can be used as an indicator of glactosemia in newborns. In an embodiment of the invention, the method can be used in the diagnosis of galactosemia in newborns. In another embodiment, the method of the invention can be used in screening for HMP related disorders such as galactosemia. In another embodiment the screening can be followed by or used in conjunction with other diagnostic methods, such as gene analysis.

Quantify or quantitative analysis, as used herein, is meant to encompass any manner of determining the relative or absolute (for instance, concentration) amount of hexose monophosphate and/or a species of hexose monophosphate in a sample. HMP level(s) as used herein also refers to both the absolute and relative amounts of HMP, as the context permits.

In the preferred embodiment, the invention provides a new rapid technique for quantitatively analysing HMP levels from a blood sample, preferably from dried blood spots, preferably on filter paper or other suitable medium, using tandem mass spectrometry (MS/MS). This new method can be used in the diagnosis of galactosemia. The new method overcomes many of the limitations in the prior art methods used for screening for the disease.

In another preferred embodiment, the invention provides a method for detecting and quantifying HMP levels in a biological sample by obtaining an HMP extract of the biological sample in a form suitable for ionization. "HMP extract" as used herein refers to an extract of the biological sample with a solvent suitable for extracting HMPs. The HMP extract does not necessarily contain any HMPs. In a preferred embodiment, the sample is extracted with a solvent that is more hydrophilic than methanol. Suitable solvents could be acetonitrile in water, tetrahydrofuran in water, methanol in water, ethyl acetate in water or isopropanol in water. More preferably the solvent is or has properties similar to that of acetonitrile in water, most preferably the solvent is 30–70% acetonitrile (v/v) in water.

In another embodiment, the biological sample is dried prior to extraction. In yet another embodiment, the biological sample is blotted onto a suitable medium, such as filter paper, dried and then extracted as above.

In another embodiment, a number of biological samples can be used in the method of the invention where applicable, such as whole blood, fractionated blood components, tissue (such as liver biopsy specimens), urine, stool, bile, saliva, sweat or other glandular secretions. Preferably, the biological sample is whole blood that is blotted onto a suitable medium, dried and then extracted.

Subsequent to extraction, the HMP extract is then ionized, using techniques such as, electrospray, or pneumatically assisted electrospray (e.g. IonSpray), to form a stream of gas phase ions. Precursor molecular ions, molecular gas phase ions having a mass to charge ratio of HMP, i.e., 259.02 Da/e, are then selected and fragmented to obtain product ions of HMP. Product ions of interest, those most indicative of HMP levels or a particular HMP, such as Gal-1-P or fructose-1-P are selected by their mass to charge ratios then detected and their ion intensities obtained. The ion intensities are preferably recorded in negative-ion mode.

The ion intensities of the product ions can be used to determine by spectrum analysis the quantitative abundance of HMPs in the biological sample; and/or to determine the concentration of HMPs, or a particular species thereof, by comparing the ion intensities of the sample with that of a control comprising a known amount or concentration of HMP or species thereof; and/or to determine the ion abundance ratios (IAR) indicating the relative amount of HMP species present within the biological sample.

In a further embodiment the method of the invention can be used to screen for and/or diagnose galactosemia in a patient by comparing the level of HMP in a blood sample with that of a cutoff level for normal individuals. In another embodiment, the invention provides a method of creating a database and a database of HMP levels (concentrations and/or IAR) of normal individuals who do not have an HMP related disorder and abnormal individuals with an HMP related disorder. In yet another embodiment, the invention provides a use of the database to determine appropriate HMP concentration and/or IAR cutoff levels useful for screening and/or diagnosis.

In another embodiment of the invention amino acids and acylcarnitines can be extracted from the dried blood samples prior to HMP extraction, using a suitable solvent, such as methanol. The methanol extract can then be removed for further analysis and the remaining biological sample can be redried and processed as above. The one biological sample, preferably blood sample, in addition to being analysed for HMP levels, can thus also be quantitatively analysed for amino acids and acylcarnitines which can be used to screen for and/or diagnose disorders in the metabolism of amino acids, organic acids, and fatty acids in the patient.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

The present invention is for a method of detecting and quantitatively analysing HMP content in a sample, preferably a biological sample and most preferably a blood sample. HMPs include, but are not necessarily limited to: Gal-1-P, glucose-1-phosphate, glucose-6-phosphate, fructose-1-phosphate, fructose-3-phosphate, and fructose-6-phosphate. The invention can be used to screen for and/or diagnose patients with or identify subjects at risk for a disorder related to abnormal levels of HMPs, such as galactose-, glucose- or fructose-monophosphates. Preferably, the invention can be used to screen for and/or diagnose patients with elevated (or excess) HMP levels.

More particularly, elevated HMP concentrations or IAR levels, insofar as they correlate with elevated Gal-1-P levels can be used as an indication of galactosemia. Other diseases which potentially might be detectable, measuring an appropriate blood and/or tissue sample include, but are not necessarily limited to hereditary fructose intolerance (OMIM 229600), fructosuria (hepatic fructokinase deficiency) (OMIM 229800), Fructose 1,6-bisphosphatase deficiency (OMIM 229700), glucose-6-phosphate dehydrogenase deficiency (OMIM 305900), and diabetes mellitus.

The method of the invention comprises a method for determining the level of HMP in a biological sample, such as whole blood, fractionated blood components, tissue (such as liver biopsy specimens), urine, stool, bile, saliva, sweat or other glandular secretions. In an example of the method, whole blood is obtained from an individual and blotted onto a suitable substrate or medium, such as filter paper that is preferably lint free and preferably having a high and homogenous capacity for absorption of liquids. The filter paper is preferably cellulose filter paper. The sample is then dried. Capillary whole blood samples blotted onto filter paper are the preferred specimen used for neonatal screening worldwide. A person skilled in the art would be familiar with suitable methods of sample collection. A sample can be collected in a variety of fashions, for instance with regard to a blood sample, the sample can be collected by: (a) direct blotting of capillary blood from an incision in the skin, (b) collection in anticoagulant-containing tubes and subsequent application onto filter paper, (c) collection in tubes with or without anticoagulant, drying and extraction being performed within the tubes, (d) collection in anticoagulantcontaining tubes and subsequent analysis of an aliquot.

In accordance with the preferred embodiment of the present invention the samples are prepared by placing an amount of the biological sample, i.e., whole blood, fractionated blood, saliva, sweat, urine, stools, bile, tissue homogenate or other glandular secretions on filter paper or other suitable material and allowed to dry preferably at about 10–100° C., more preferably at room temperature, preferably at 19–26° C. The filter paper is preferably cellulose filter paper, but other types of substrates may be applicable. Liquid samples in tubes, such as anticoagulated whole blood, fractions of blood, saliva, urine or tissue homogenates may be applicable as well. The amount blotted on the filter paper is typically in the range of 50–100 $\mu$l and preferably about 75 $\mu$l.

After drying, a fixed amount (typically a circular disc of 3.2 millimetre diameter, typically representing about 3.5 microlitres of sample) of dried blood filter paper sample is punched from the filter paper and placed in a microtiter plate or other suitable vesicle. HMP from the dried blood sample is extracted using a solvent suitable to extract HMP, preferably Gal-1-P. A solvent suitable to extract HMP in one embodiment is a polar solvent. In another embodiment, the solvent is preferably more hydrophilic than methanol. Preferably it is miscible in water. Water is preferably present to ensure sufficient polarity. Examples of suitable solvents are, but are not limited to, solvents with properties similar to: acetonitrile in water, preferably 30:70 to 70:30 (v/v), preferably 1:1 (v/v). Other suitable solvents could comprise ethyl acetate in water, tetrahydrofuran in water, methanol in water or isopropanol in water. Most preferably the extraction buffer is acetonitrile:water (1:1) (v/v). The filter paper is incubated with about 50–1000 $\mu$l and preferably with about 150 $\mu$l of extraction buffer for about 5–100 minutes, and preferably 20 minutes, at preferably about room temperature. A person skilled in the art would appreciate that other temperatures might be applicable, however, room temperature is preferred as it is convenient and does not create problems with solvent loss by evaporation.

A sample of the resulting solution or extract, preferably about 100–200 $\mu$l s is preferably centrifuged to remove debris (i.e., about 1800–10000 g for 10 minutes) and then subjected to tandem mass spectrometry for quantitative analysis of HMP in the sample, which ionizes the solution, desolvates the ions, and then isolates and detects ions and their fragments by their mass-to-charge ratio. Prior to ionization, the sample can optionally be subjected to liquid chromatography to get rid of particulate debris, or interfering or signal-suppressing components in the extract.

It should be noted that although a specific method of sample preparation is described herein, a person skilled in the art would appreciate that any form of sample preparation, suitable for HMP detection and analysis by a mass spectrometer used to carry out the method, would be suitable. For example, the method for sample preparation may vary with the nature of the sample (i.e., blood, or saliva or tissue) and/or the type of mass spectrometer used.

In one embodiment of the invention, the dried, preferably, blood, sample of the invention, prior to extraction with a solvent suitable for extraction of HMPs, can be pre-extracted with another solvent suitable to extract components other than HMP, such as to extract amino acids and acylcarnitines (e.g. methanol). This resulting extract can itself be analysed to screen for disorders associated with certain amino acid or acylcarnitine levels. For instance elevated phenylalanine levels can indicate phenylketonuria. An analysis can be done in accordance with Rashed et al (10), to screen for phenylketonuria. The same pre-extracted dried blood spot can then be recovered, dried, preferably under nitrogen, and extracted with a solvent suitable to extract HMPs as noted above, to screen for HMPs as described above. Thus, in a preferred embodiment, the present invention also provides a rapid method wherein one dried blood spot can be used to screen for both HMP related disorders, such as galactosemia and diseases related to abnormal levels of amino acids and acylcarnitines, such as metabolic disorders of amino acids, organic acids and fatty acids, e.g. phenylketonuria.

Mass Spectrometry

The preferred method of analysing HMP levels of the invention is by tandem mass spectrometry.

A tandem mass spectrometer first ionizes particles and then separates them based on their mass-to-charge ratio (m/z). A tandem mass spectrometer has at least two mass filters, preferably quadrupole filters placed in tandem. The first mass filter ($Q_1$) is set to transmit the precursor ion mass-to-charge ratio, which in the case of HMPs is about 259.02 Da/e. Transmitted ions are led into a collision cell ($Q_2$) containing an inert gas, such as nitrogen. When the selected ions collide with gas molecules, they fragment and generate product ions. The second mass filter ($Q_3$) is set to transmit selected product ion mass-to-charge ratios to the detector [Selected Reaction Monitoring (SRM)]. The ion intensity of the product ion can then be determined using techniques known in the art. The HMPs have three predominant product ions, $[PO_3]$, $[H_2PO_4]^-$, and $[(C_2H_3O)HPO_4]$, with respective mass-to-charge ratios of about 78.96 Da/e, 96.97 Da/e, and 138.98 Da/e (15). A person skilled in the art will appreciate that the m/z values provided herein may vary slightly depending on how the molecular mass is calculated or the tandem mass spectrometer is calibrated.

Many tandem mass spectrometers also have a fragmentation section or collision cell between first and second mass filters. The fragmentation section is usually a quadrupole mass filter operated in the radio frequency (RF) only mode as an ion containment device and containing a collision gas at a pressure of approximately 3 millitorr. The first and second mass filters are then quadrupoles on either side of the fragmentation section. In a triple quadrupole instrument, the quadrupoles are commonly designated $Q_1$, $Q_2$, and $Q_3$, with $Q_2$ being the fragmentation section or collision cell. It is also possible to use a so-called time-of-flight (TOF) instrument, where the third quadrupole $Q_3$ is a replaced by a TOF section. However, many other tandem or other mass spectrometers are known, including various combinations of analysers and quadrupole filters and could be used to effect the method of the present invention. Possible configurations include ion traps, TOF-TOF, Q-TOF, TOF with post-source decay, mass-analyzed ion kinetic energy spectroscopy (MIKES), quadrupole ion trap, Fourier Transform Ion Cyclotron Resonance Mass Spectrometry (FTICR) and other methods capable of generating product ion spectra after pre-selection of precursor ions.

There are various means to ionize particles, such as electrospray (ESI), pneumatically assisted electrospray ionization, (such as, IonSpray) liquid secondary ion (LSI), fast atom bombardment (FAB), fast ion bombardment (FIB), and pulsed ionization sources such as matrix-assisted laser desorption ionization (MALDI). The preferred method of the present invention is electrospray ionization (ESI), and pneumatically assisted electrospray ionization (e.g. IonSpray).

Although, it is not currently possible to determine from a sample containing unknown amounts of HMPs, how much of each ionization fragment or product ion represents Gal-1-P specifically, it has been determined that the $[PO_3]$, fragment is most abundant and is most indicative of Gal-1-P levels in a sample. It is thus the fragment preferably used in diagnosis of galactosemia. The $[H_2PO_4]^-$ fragment or product ion is most indicative of fructose-1-phosphate levels and is thus the fragment preferably used in the diagnosis of disorders related to fructose-1-phosphate levels. Thus the preferred product ions of interest used to screen or diagnose for an HMP related disorder may vary depending on the disorder Further, it has been found that feeding infants intravenously with an equimolar mixture of glucose and fructose does not give rise to elevated concentrations of HMPs as measured by the invention.

Standards and Diagnostic Applications:

Different standardisation techniques to calibrate results and minimize false positives and negatives are contemplated by the invention. For instance, one can use an external standard, adding known amounts of HMP, preferably Gal-1-P, to a sample of whole blood collected from a healthy individual and blotted onto filter paper under conditions (low temperature, i.e., from 1–25° C., preferably from 19° C.) in which GALT activity is inhibited. This external standard array can be processed identically to the test samples at each analytical run.

Internal standards can also be used. For instance, the present inventors have analysed the potential of the ion abundance ratio (IAR) of the SRM transitions 259.02–78.96 and 259.02–96.97, i.e., the ratio of the signal intensity of fragment 78.96 Da/e to the signal intensity of fragment 96.97 Da/e, both derived from the precursor ion 259.02 Da/e. This IAR has an equal screening performance (100% sensitivity and 100% specificity) as does the calculated concentration of HMPs determined from an external standardisation curve using the 78.96 Da/e fragment.

Further, an isotopically labelled internal standard for Gal-1-P could be used as an internal standard. In principle, any HMP labelled with stable isotopes giving a mass increase, preferably of 3 Da or more over unlabeled Gal-1-P would be suitable. To prevent signal interference from a labelled internal standard, it might be preferable to position the label on the phosphate group, since one would get mass increases on both precursor and product ions. This could also allow assessment of possible hydrolysis of the internal standard, which would generate a labelled phosphate group.

Elevated levels of HMP can be determined by comparing the concentration of HMPs (or respective parent or relevant product ions) or the IAR of the patient with that of a cutoff level characteristic of the HMP disorder, i.e galactosemia. Appropriate cutoff levels can be determined from HMP concentrations or IAR levels seen in normal individuals and those with an HMP indicative disorder, such as, galactosemia patients. A database of normal and abnormal HMP concentrations or IAR levels can be developed from quantitative analysis of samples according to the method of the present invention of subjects who are known to have or not to have the disorder. HMP concentrations or IAR levels characteristic of normal and galactosemia patients are determined and diagnostic cutoff values determined accordingly. The database can be continually updated. A method for creating such a database is also intended to be encompassed within the scope of this invention. Elevated concentrations of HMPs or elevated IAR correlate with elevated levels of Gal-1-P and thus enable presumptive diagnosis of galactosemia.

The current inventors have determined that HMP levels above 0.94 millimolar or 1.41 IAR are potentially indicative of galactosemia. However, most indicative are HMP levels between 2.6 and 5.2 millimolar or 1.69–1.76 IAR, since this range contains all averaged patient concentrations in the examples determined by external standardisation using the 78.96 Da/e fragment. Therefor the cutoffs for galactosemia according to the examples could be between 0.95 to 2.5 mmol/l for HMP concentration and 1.42 to 1.68 IAR., more preferably from 0.95 to 1.43 mmol/l for HMP and 1.42 to 1.56 IAR if detection is desired of individuals who are compound heterozygous for a GALT null allele and the Duarte allele. The inventors recommend that the preferred cutoffs for neonatal screening determined by analysis of data would be 1.2 millimolar or 2.0 millimolar HMP (1.49 or 1.63 IAR), depending on whether or not compound heterozygotes for a partially disruptive mutation in the GALT gene (Duarte mutation) and a fully disruptive mutation should be detected or not. The lower HMP concentration and IAR value would allow for detection of galactosemia patients as well as compound heterozygotes carrying a partially disruptive GALT allele (Duarte allele) and a fully disruptive GALT allele. The higher the HMP concentration and higher IAR value would allow detection of individuals with fully inactivated GALT genes on both alleles, i.e., galactosemia patients.

A similar method can be used to determine appropriate cutoff levels for other HMP related disorders.

The screening methods of the invention outlined herein can be used alone or preferably in conjuction with other diagnostic indicators. The method of the invention can be used for screening individuals for further diagnostic follow-up such as gene analysis.

The following non-limiting examples are illustrative of the present invention:

EXAMPLES

Introduction

The following examples describe a method to quantify the content of HMP in neonatal blood filter paper samples.

Instruments and Materials

The following instruments and materials were used in the examples that follow.

Instruments:

(a) Puncher Wallac, Delfia dried blood spot puncher 1296-071, serial no. LR52500, diameter of punch head: 3.2 mm (b) 8-channel pipette, Labsystems F 24449, serial no. 4510

(c) PE-Sciex API 365 tandem mass spectrometer with IonSpray source, (Perkin Elmer-Sciex, Toronto, Canada, serial no. 0029712PT)

(d) Perkin-Elmer series 200 autosampler, The Perkin Elmer corporation, Norwalk Conn., USA. serial no. 293N8040613).

(e) Shimadzu LC-10Avdp pump. Shimadzu corporation, Kyoto, Japan, part number 228-39000-92, serial no. C20963502470.

(f) Power Macintosh G3 computer, serial no. XB81303HBBW (g) Neo Chrom software, version 1.0 g.

(h) Analytical weight, Sartorius, serial no. 71004423, Kebolab, Denmark.

Materials (a) Galactose-1-phosphate (Cat. No. G-0380, Lot no. 32H7030). Glucose-1-phosphate (Cat. No. G-6875, and fructose-1-phosphate (Cat. No. F-1127) were purchased from Sigma Chemical Co.

(b) Acetonitrile. Aldrich, Cat. no. A/0627/15.

(c) Ultra-High-Quality (UHQ) water. From Millipore Milli-Q A10, (in-house system).

(d) Sealing film for microtiter plates. Nunc, Cat. No. 236366.

(e) Polystyrene microtiter plates, conical bottom wells. Nunc, Cat. No. 245128.

(f) Extraction/running buffer: 500 ml UHQ-water and 500 ml of acetonitrile. Filtered on 0.45 $\mu$m nylon-66 filters (Varian Chromatography Systems) and degassed by sparging with helium.

(g) Filter paper. Schleicher and Schuell, cat. no. 2992.

(h) EDTA vials, Venoject, VT-100TK, 0.1 ml EDTA 0.47 M, Lot nr. 97I22L7.

(i) Sample glass, WR 1270, 14.5×100 mm. Thüringer Pharma glass, Germany.

Materials and Methods

Reagents

Galactose-1-phosphate, glucose- and fructose-1-phosphate were purchased from Sigma, (Sigma Chemical Co., St. Louis, USA). The extraction solution/mobile phase was a 1:1 mixture of ultra high quality water from an in-house Milli-Q system (Millipore, USA) and acetonitrile (Aldrich, USA). Before use, the solution was filtered on 0.45 $\mu$m nylon-66 filters (Varian Chromatography Systems) and degassed by sparging with helium.

Subjects and Blood Samples

Twenty-two patients diagnosed with galactosemia in the period 1984–1998 were identified from the medical records at the Department of Clinical Genetics, Rigshospitalet University Hospital, Copenhagen, Denmark. All diagnoses were confirmed by GALT genotype analysis. The Danish neonatal screening program utilizes dried blood spot samples (DBSS) collected on Schleicher & Schuell 2992 filter paper, typically obtained 5 to 7 days postnatally. Subsequent to routine analysis, the DBSS are stored at 20° C. in a biological specimen bank (7). Residuals of the primary DBSS were available from 12 galactosemia patients. A reference group was established by collecting 2055 random, de-identified DBSS residuals from apparently healthy infants 7–10 days after their sample had been analysed by the routine neonatal screening program. Information on the birth weight and postnatal age at the time of blood sampling was retained from the blood sample data form. A carbohydrate infusion group consisted of samples from neonatal intensive care patients receiving intravenous fluids containing 5% (w/v) glucose and 5% (w/v) fructose in combination. This group was evaluated anonymously by creating DBSS from surplus EDTA blood drawn for routine clinical chemistry tests during carbohydrate infusions. A hexose-monophosphate (HMP) stability group consisted of random DBSS that had been stored at 20° C. for 1, 2, 5 and 10 years (160 samples for each duration of storage).

External Concentration Standards

Stock solutions with different concentrations of Gal-1-P were prepared in 0.9% (w/v) NaCl in water solution. Blood was collected in EDTA-vials from a healthy fasting adult female. The blood was cooled to 4° C. in order to repress endogenous GALT activity. From each stock solution of Gal-1-P, 70 ml were added to 1930 ml prechilled blood. The mixtures were inverted gently. Blood spot concentration standards were prepared by pipetting 75 $\mu$l spiked blood onto filter paper (Shleicher & Schuell, cat no. 2992). The standards were dried over-night at room temperature and were subsequently stored in zip-lock plastic bags at 20° C. The standards contained the following concentrations of added Gal-1-P: 0; 0.0625; 0.125; 0.25; 0.50; 1.0; 2.0; 4.0; 8.0 mM. The stability of Gal-1-P during the preparation of external standards was examined by assaying DBSS created from EDTA-blood spiked with 0.0625 mmol/l Gal-1-P that had been pre-incubated for up to 21 hr at 4° C. or at room temperature before spotting onto filter paper.

Extraction of Galactose-1-Phosphate

To determine the optimal composition of the solvent used to extract Gal-1-P from DBSS, different mixtures were tested of acetonitrile and water, methanol and water, and methanol and acetonitrile with either solvent in a pair ranging in concentration from 10–90% v/v in steps of 10%. The extraction solvents were used to prepare extracts of a 0.5 mmol/l Gal-1-P concentration standard in microtiter plates, as described in the sample preparation section, with the following modification: to eliminate effects of solvent composition on desolvation and ion formation, all extracts were evaporated at 45° C. under a gentle stream of nitrogen gas and were redissolved in acetonitrile:water 1:1, injected into the tandem MS instrument, and counted as described.

Sample Preparation

From each DBSS, one disc with a diameter of 3.2 mm was punched into a blank well in a conical bottom microtiter plate. Extraction solution (150 $\mu$l) was added to each well using an 8-channel pipette, and the plates were sealed with adhesive film (Nunc, Sealing tape SI, cat. 236366). Extraction was carried out by gentle rotation on an orbital shaker for 20 min, and 100 $\mu$l-aliquots were transferred to fresh microtiter plates which were sealed with adhesive film. Filter paper lints were pelleted by centrifugation at 1800 g for 10 min to prevent blockage of the autoinjector port and tubing system.

The microtiter plates were loaded with the external standards array in triplicate. Patient samples were measured in duplicate, samples from the carbohydrate infusion group were measured in triplicate. Each measurement from the standards array, the patients, and the carbohydrate loading group was preceeded by a blank sample (extraction solution) to avoid any possibility of sample carry-over. Samples from the reference group were assayed as singletons without separation by blanks. Every 20th sample of an assay was a control sample containing 0.5 mmol/l Gal-1-P. Processed microtiter plates were loaded in a Perkin-Elmer Series 200 autosampler (Perkin-Elmer Corporation, Norwalk, USA) fitted with a Peltier cooling element set at 4° C. Preparation of 300 samples typically took 1–1.5 hr including punching.

Tandem Mass Spectrometry

All measurements were carried out on a API-365 tandem mass spectrometer (PE-Sciex, Toronto, Canada) fitted with an electrospray source (IonSpray).

Figure 4:
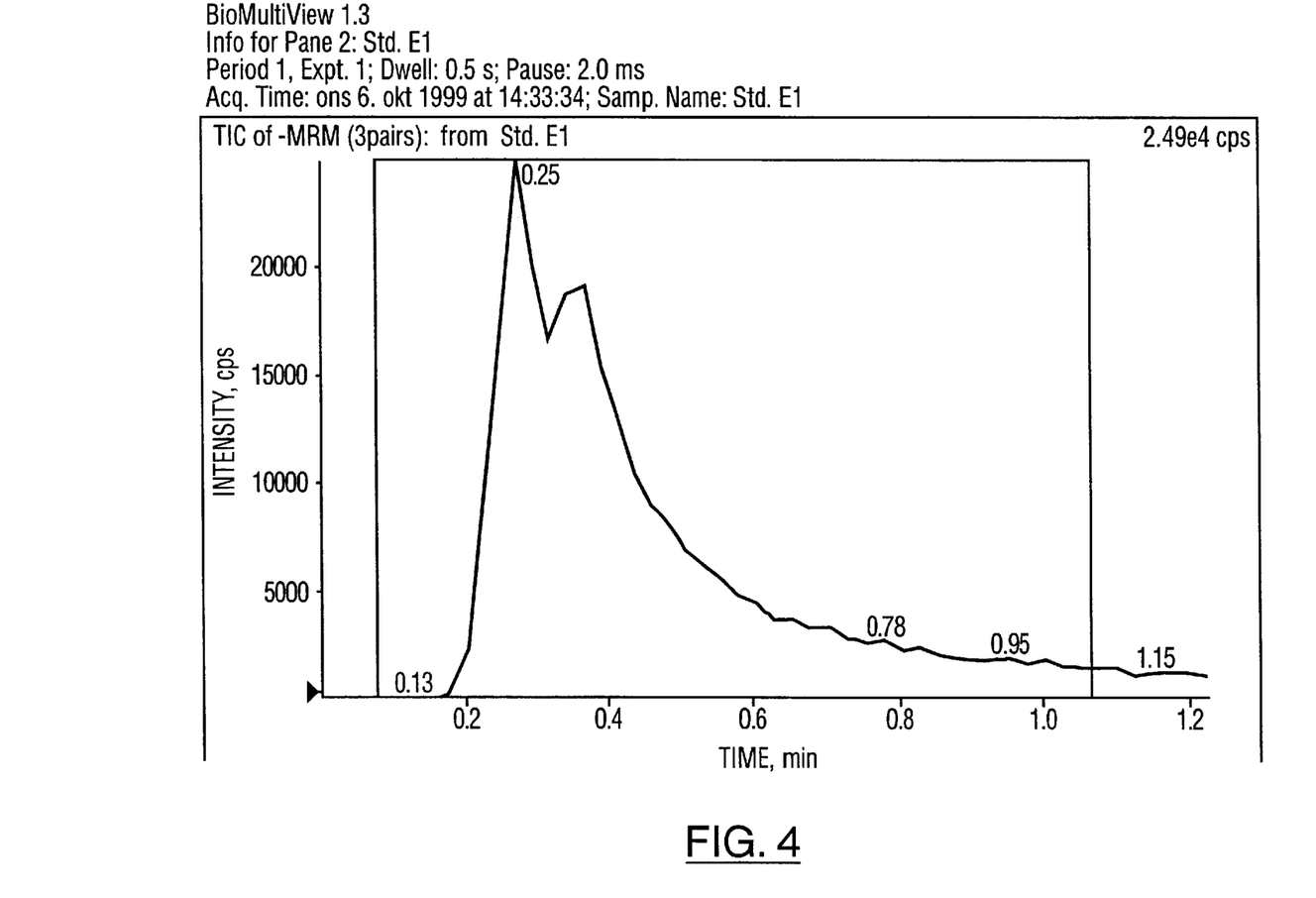
FIG. 4 is a total ion current chromatogram (TIC) representing the ion intensities obtained by measuring a sample of HMP being injected into the tandem mass spectrometer. The TIC is derived by summation of signals from cyclic measurements of the three ionized fragments of HMP.
Figure 5:
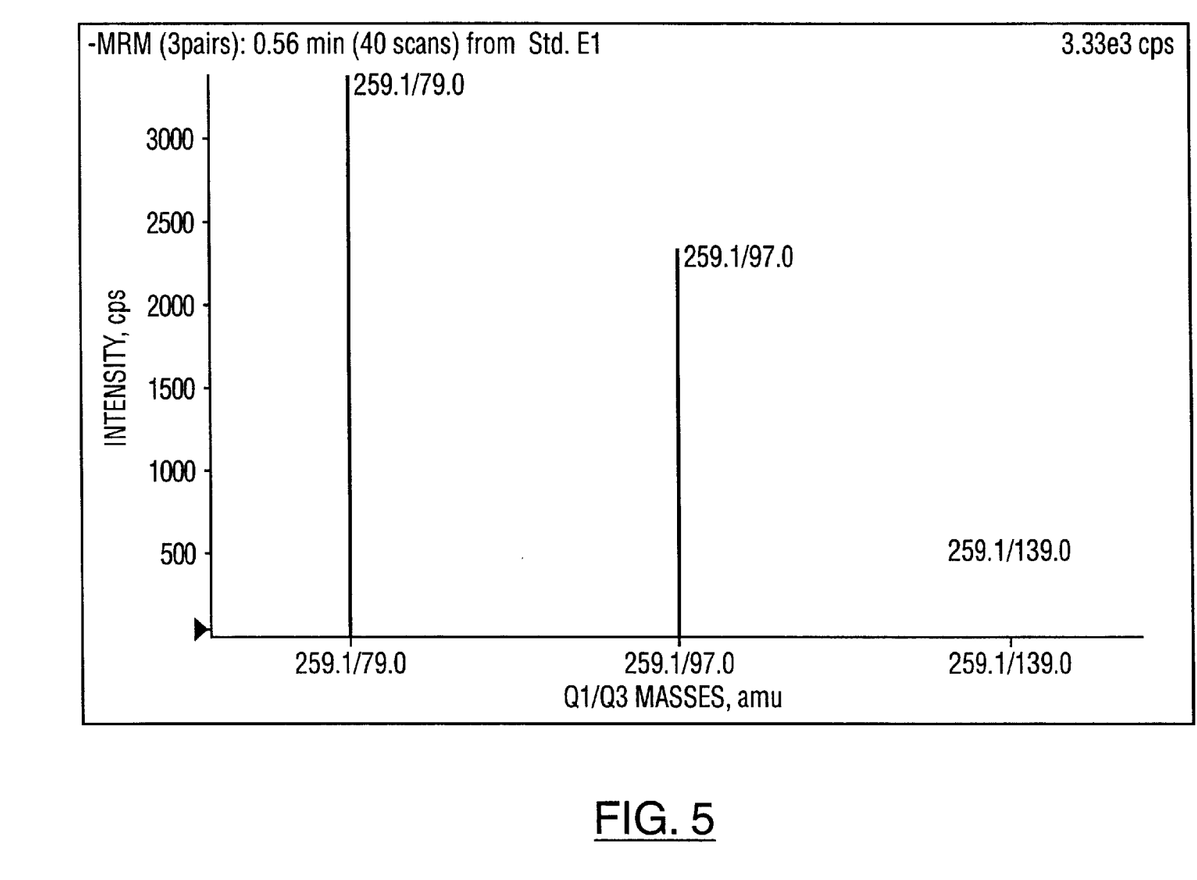
FIG. 5 shows a histogram plot of the average ion intensity of each of the three fragment ions measured in the hatched time frame on FIG. 4. Further, the figure indicates the mass-to-charge settings used to detect the fragment ions of interest.

It was determined that all deprotonated HMPs (259.02 Da/e) studied undergo collision-induced dissociation into three predominant fragment of 138.98 Da/e, 96.97 Da/e, and 78.96 Da/e, which were measured as interlaced selected reaction monitoring (SRM) functions in the following applications:

A) For the study of the fragmentation patterns of Gal-1-P, glucose-1-phosphate, and fructose-1-phosphate, 20 $\mu$mol/l solutions of each substance dissolved in mobile phase were infused at 15 $\mu$l/min to the tandem MS instrument. Twenty multiple channel addition scans were collected with the instrument settings indicated below. (For instance as indicated in FIGS. 4–5, and in the Appendix hereto.

B) For analysis of processed DBSS, 8 $\mu$l of each sample extract was injected into a constant flow of 70 $\mu$l/min mobile phase delivered by a Shimadzu LC-10 Advp pump (Shimadzu Corporation, Kyoto, Japan), and the SRMs were monitored during the injection cycle. The application was run with a sample-to-sample cycle time of the order of 1.5 min, but this interval could be shortened considerably if higher flow rates were to be used.

Throughout, the instrument was operated in negative ion mode with a needle voltage of −4.9 kV, collision energy of −25 eV, nitrogen collision gas at setting 2 (manufacturer's units), and dwell time 500 ms for each SRM.

Data Processing

Ion intensities were extracted from the raw data files using Neochrom Software, version 1.0 (PE-Sciex) operating on a Macintosh Power PC platform. Microsoft Excel version 5.0c for Windows was used to generate standard curves by linear regression, using the signal obtained from the 259.02/78.96 ion transition for standardisation, except where noted. The equations describing the standard curves were used to calculate the content of HMP in analyzed samples. The ion abundance ratio (IAR) of transition 259.02/78.96 relative to transition 259.02/96.97 was calculated for each sample.

Statistical Methods SPSS version 9.0 software was used for statistical analysis. Mann-Whitney U test was used to compare variables between groups. Spearman's rank correlation test was used to investigate correlations. One-way ANOVA was used to determine intra- and inter-assay coefficients of variation (CVs). Linear regression analysis was used to determine confidence intervals and standard error of the estimate for the calibration curves. All tests were 2-tailed and were considered statistically significant if $p<0.05$ for the null hypotheses.

Analytical Precision

A control sample (0.5 mmol/l Gal-1-P concentration standard) was quantified 57 times in 8 separate assays, and CVs were determined by one-way ANOVA.

Genotype Analysis

The GALT genotype of a sample from the reference group which had an extreme HMP concentration and IAR was determined by restriction analysis of polymerase chain reaction-amplified DNA extracted from the DBSS residue.

Results

Fragmentation Pattern of Hexose Monophosphates

Figure 1:
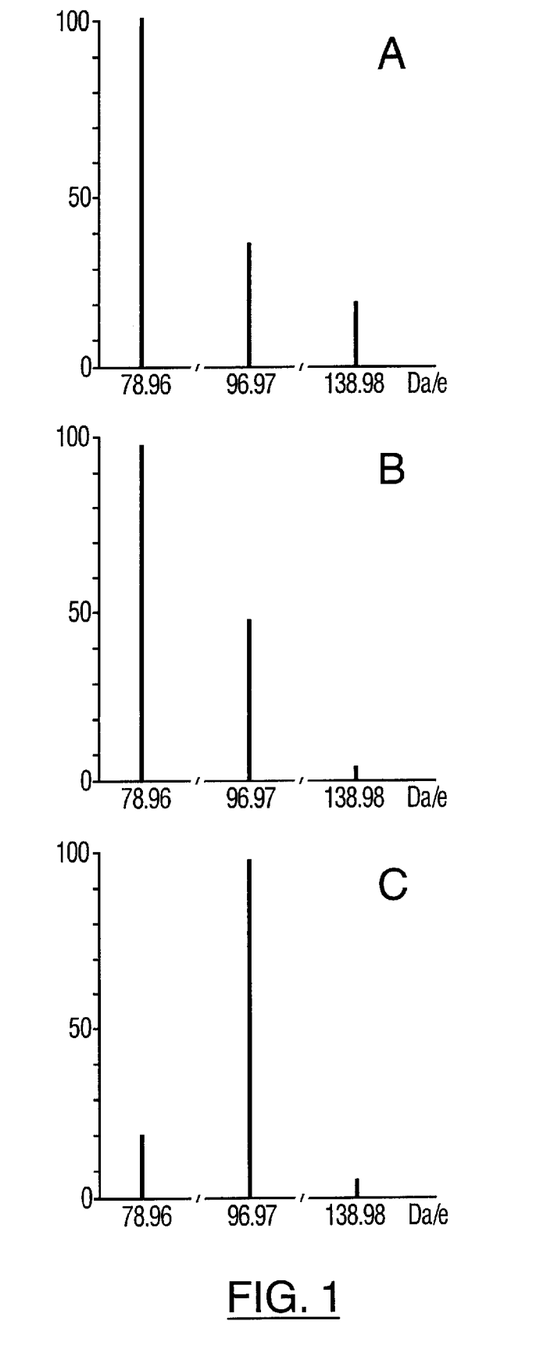
FIG. 1 shows the three predominant fragment ions of glucose-1-phosphate (panel 1A), galactose-1-phosphate (panel 1B), and fructose-1-phosphate (panel 1C).

Tandem mass spectral analysis demonstrated that deprotonated HMPs (259.02 Da/e) dissociate into three predominant fragments of 138.98 Da/e, 96.97 Da/e, and 78.96 Da/e, in agreement with previous findings (15). The predicted structures of the fragments are $[(C_2H_3O)-HPO_4]^-$, $[H_2PO_4]^-$, and $[PO_3]^-$, respectively. There are marked differences in the relative abundance of fragments 78.96 Da/e and 96.97 Da/e depending on the structure of the HMP (FIG. 1). For aldosemonophosphates (glucose-1-phosphate and Gal 1 P) the signal of the 78.96 Da/e fragment predominates (FIG. 1, panel A and B), while the 96.97 Da/e fragment predominates for fructose-1-phosphate, a ketose monophophate (FIG. 1, panel C).

Extraction of Galactose-1-Phosphate

The optimal extraction solvent was determined to be 30–70% acetonitrile in water (v/v) which, throughout the indicated concentration range, yielded 3- and 9-fold higher ion intensities than the optimal signal from samples extracted with methanol:water and methanol:acetonitrile mixtures, respectively (data not shown). Thus, acetonitrile:water 1:1 (v/v) was used for extraction in all further applications.

External Standardisation

Figure 2:
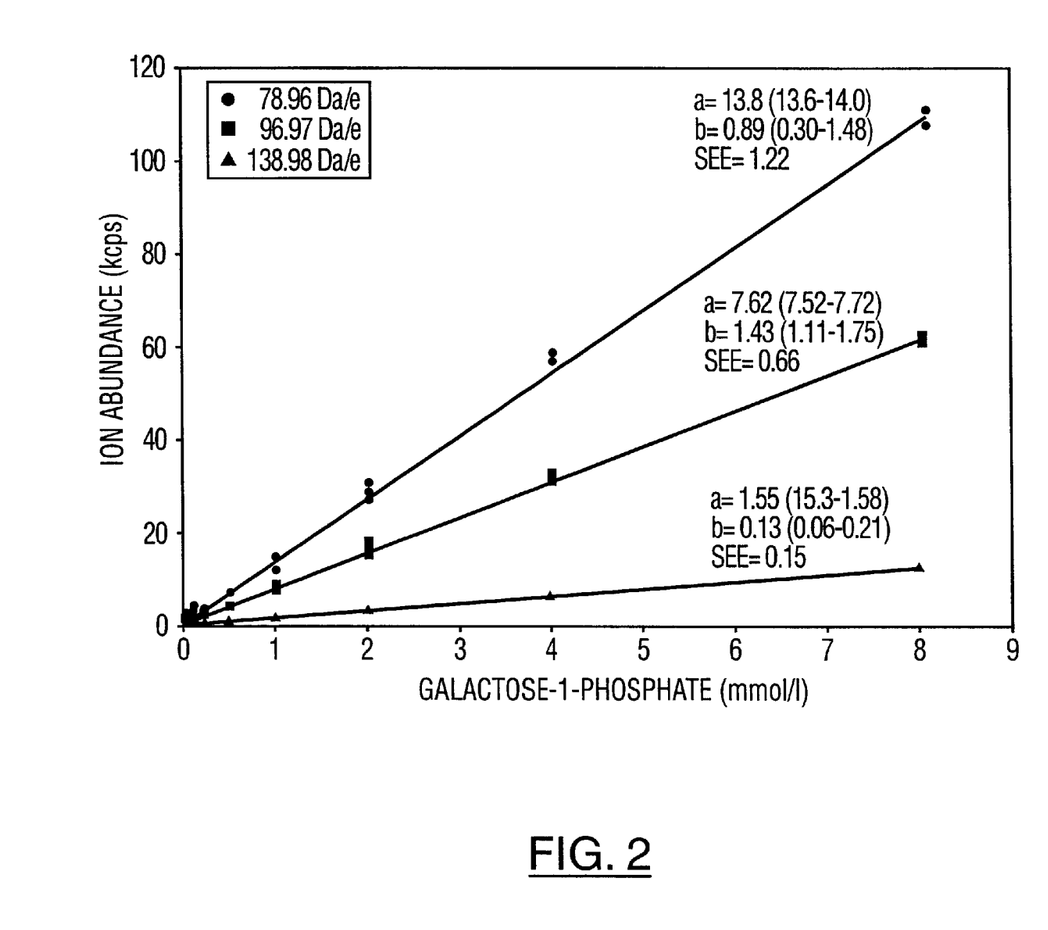
FIG. 2 is a standard curve from triplicate measurements of nine different standard bloodspots, ranging from 0 to 8 mmol/l added concentration of Gal-1-P. The signal intensity of three different fragment ions of the HMP precursor ions (259.02 Da/e) is shown for each concentration. The fragments ions are 78.96 Da/e, 96.97 Da/e, and 138.98 Da/e. Linear regression analysis was used to derive slopes (a), intercepts (b), and standard error of the estimates (SEE).
Figure 3:
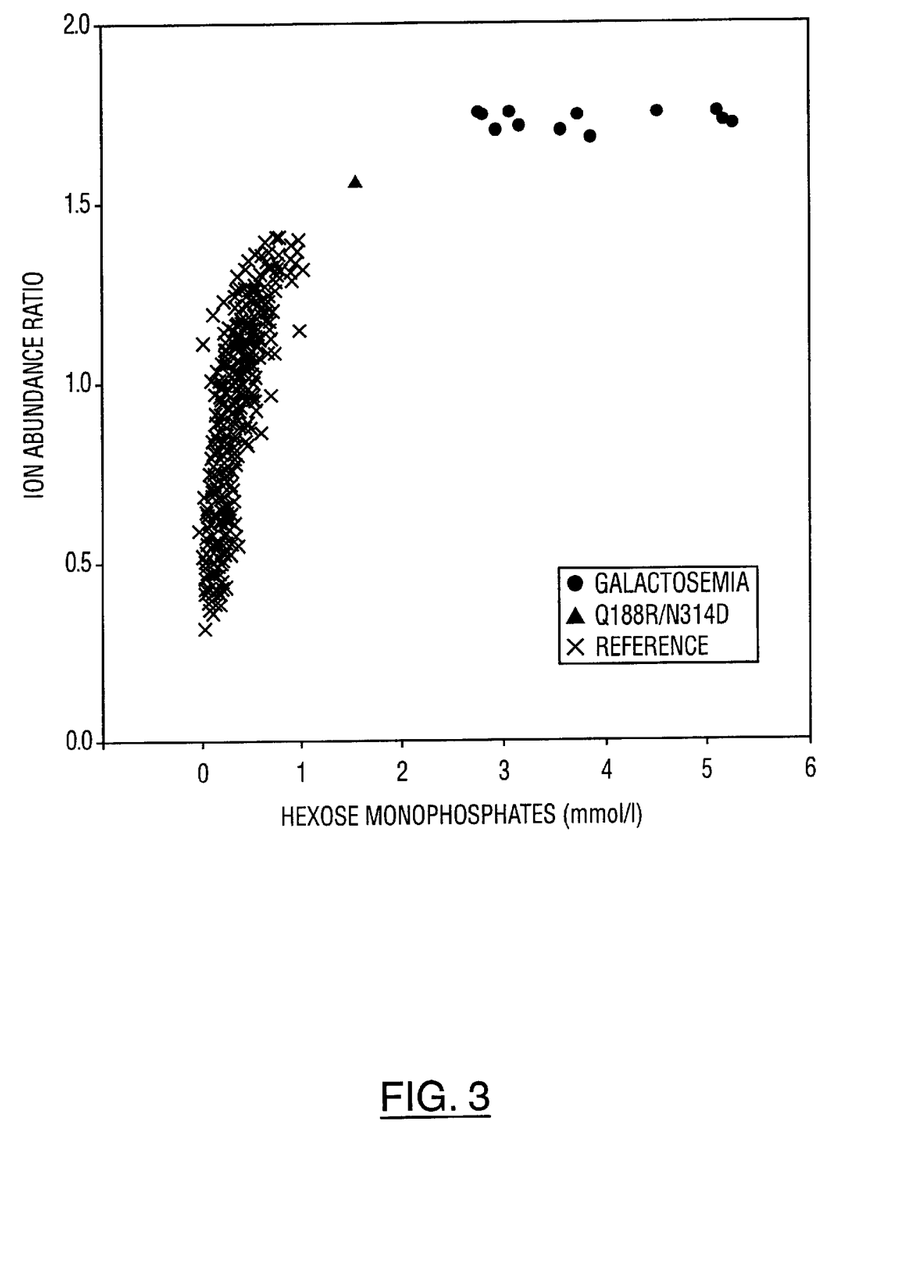
FIG. 3 is a scatter plot comparing the hexose-monophosphate concentration and ion abundance ratio (IAR) in samples from patients with galactosemia, a Q188R/N314D compound heterozygous individual with reduced GALT activity, and the reference population. It illustrates that the IAR has an equal screening performance (100% sensitivity and 100% specificity) as does the calculated concentration of HMPs determined from an external standardisation curve using the 78.96 Da/e fragment. It should be noted that all three HMP fragments could be used for quantification by external standardisation. The 78.96 Da/e fragment was selected because it gives the highest signal intensity.

The ion intensities of the three predominant HMP fragments were plotted against the concentrations of added Gal-1-P (FIG. 2). In all experiments, all three fragments produced linear standard curves ($r^2=0.994$ to $1.000$) within the range 0 to 8 mmol/l of added Gal-1-P. Standard curves derived from the 96.97 Da/e fragment exhibited detrending towards higher ion intensitites in the low range (<0.0625 mmol/l) of added Gal-1-P. Furthermore, computed HMP concentrations in neonatal screening samples were 0.1 mmol/l higher on the average when the 96.97 Da/e fragment was used for standardisation vs. when the 78.96 Da/e or 138.98 Da/e fragments were used for standardisation. This difference was abolished in the low (<0.0625 mmol/l) HMP concentration range. The differences in calculated HMP concentrations could be due to a higher ratio of ketose monophosphates to aldose monophosphates or higher levels of interfering compound(s) in neonatal screening samples, relative to the adult blood which was used to generate the external concentration standards. There was no significant difference between HMP concentrations determined by standardisation using the 78.96 Da/e or 138.98 Da/e fragments. Over-night incubation at 4° C. or at room temperature of freshly drawn EDTA-blood spiked with Gal-1-P showed no evidence of signal degradation (data not shown), as would be expected since Gal-1-P was added to the extracellular compartment and would not be exposed to intracellularly localized GALT. For all categories of samples, the ion abundance of the 78.96 Da/e fragment was 7–9 fold higher than that of the 138.98 Da/e fragment on the average, while the IAR of the 78.96 Da/e fragment relative to the 96.97 Da/e fragment varied with disease state, being highest in galactosemia patients (FIG. 3). It was decided to use the ion intensity of the 78.96 Da/e fragment for quantification of Gal-1-P since it was associated with a Gal-1-P fragmentation pattern (FIG. 1) and gave the highest signal intensity in samples containing excess Gal-1-P (spiked concentration standards and galactosemic samples).

Analytical Precision

Intra- and interassay CVs at an average HMP concentration of 0.54 mmol/l were determined to be 11% and 13%, respectively. For IAR, the intra- and interassay CVs at 1.44 units were 1.5% and 4.1%, respectively. Total analytical precision derived by quadratic summation of intra- and interassay CVs were thus 17% (HMP concentration) and 4.4% (IAR).

Stability of Hexose Monophosphates

Analysis of DBSS which had been stored for varying lengths of time at −20° C. revealed minor but statistically significant alterations in HMP status. Thus, the median HMP content declined from 0.15 to 0.12 mmol/l ($p=0.001$) over the course of 10.6 yrs, while the IAR increased from 0.80 to 0.84 ($p=0.01$). No appropriate curve fitting models were apparent for either association, and the changes were considered to be too minor to necessitate correction of results obtained from the analysis of archival patient samples.

Reference Group

The median concentration of HMP in 2055 reference samples was 0.15 mmol/l (−0.08–0.94 mmol/l) (FIG. 3). The median IAR of fragment 78.96 Da/e relative to 96.97 Da/e was 0.80 (0.32–1.41). Neither HMP concentration nor IAR correlated with postnatal age at blood sampling or birth weights $\geq 2500$ g. For low birth weight (<2500 g) infants (n=114), however, both HMP concentration and IAR correlated positively with the birth weight ($p<0.01$ and $p<0.05$, respectively). One sample with an extreme HMP concentration of 1.44 mmol/l and an IAR of 1.57 was shown by DNA mutational analysis to be compound heterozygous for the Duarte (N314D) and Q188R mutations in the GALT enzyme, and was excluded from the reference group.

Galactosemia Patients

Characteristics of patient samples are shown in table 1. HMP concentrations ranged from 2.6 to 5.2 mmol/l, and the IAR ranged from 1.69–1.76. There was a weak correlation between postnatal age at blood sampling and HMP concentration (p<0.05), but no other correlations between the parameters listed in Table 1.

Carbohydrate-Infused Neonates

The intensive care neonates received infusions of a 5% glucose (w/v) and 5% fructose (w/v) solution at a median rate of 191 (12–312) ml/24 hr. Compared with the reference group, the carbohydrate loading group (n=10) had slightly, but significantly repressed levels of HMP and IAR (medians, 0.062 mmol/l and 0.42, respectively, p<0.001 for both comparisons). There was, however, no difference in HMP concentration when the 96.97 Da/e fragment was used for standardisation. The rate of carbohydrate infusion correlated negatively with the IAR (p<0.001), but not with HMP concentrations.

Diagnostic Accuracy

FIG. 3 compares the patient group with the compound heterozygote and the reference group for HMP concentration and IAR. For neonatal screening, cutoffs in the range 0.95–2.5 mmol/l for HMP concentration and 1.42–1.68 for IAR yield sensitivities and specificities of 100%. If detection of Q188R/N314D compound heterozygotes is desired, 100% sensitivity and specificity can be obtained with cutoffs in the range 0.95–1.43 mmol/l for HMP and 1.42–1.56 for IAR. The latter ranges are both equivalent to 2 standard deviations of the respective tests, based on the total analytical precisions.

Screening for Amino Acids, Acylcarnitines and HMPs Using the Same Dried Blood Spot The present inventors also made two sequential extractions of the same dried blood spot with success. The first extraction was carried out with methanol containing internal standards of amino acids and acylcarnitines as described by Rashed et al (10). The amino acids and acylcarnitines values were measured by tandem mass spectrometry, and calculated by a computer algorithm. (See Table 1) The remnant blood spots were dried down by a flow of nitrogen, and subjected directly to the second extraction procedure described herein for HMPs. This second hydrophilic extraction has been proven to give the same result, as if the extraction was carried out on a fresh blood spot.

The inventors have developed a novel test applicable to neonatal screening for galactosemia. The test principle is quantitative analysis of HMP or an HMP fragment ion(s) indicative of Gal-1-P by tandem MS. The method of the invention can be adapted to screen for other HMP related disorders, i.e., by detecting and quantifying HMP ions indicative of the disorder. For optimum results, in order to determine whether the subject has a problem in metabolising Gal-1-P in accordance with the galactosemic screening method of the present invention, subjects have to be exposed to a galactose-containing diet before screening. Thus, parenteral nutrition, which does not contain galactose, or sampling prior to effective lactation can create false negative screening results as can blood transfusions and other measures which reduce the blood content of Gal-1-P. These limitations, however, are also present with other assays for Gal-1-P and for galactose. The present assay is insensitive to problems of enzyme inactivation.

Concentrations of HMP calculated by external standardisation using the 78.96 Da/e fragment correlated with Gal-1-P concentrations (FIG. 2) and with galactosemia (FIG. 3). There was no overlap in HMP concentrations between a cohort of 2055 reference samples and 12 patients, yielding a diagnostic sensitivity and specificity of 100%. Carbohydrate infusions did not cause elevations of HMP or IAR in neonatal intensive care patients. A sample from the original reference cohort contained an elevated concentration of HMP at 1.44 mmol/l, clearly separable from both the reference cohort and the patient cohort. Genotyping revealed compound heterozygosity for a fully GALT-inactivating mutation (Q188R) and for the partially disruptive Duarte mutation (N314D). Subjects with this genotype only have 5% of normal GALT activity and are recommended to have dietary treatment during the first year of life (12). A cutoff of 1.2 mmol/l HMP for neonatal screening is therefore suggested. This would detect galactosemia patients with a sensitivity and specificity of 100% and presumably include most compound heterozygotes recommended for treatment.

Furthermore, the IAR between fragments 78.96 and 96.97 Da/e was able to distinguish clearly between the reference cohort, the compound heterozygote, and the patient cohort, with marked elevations in the latter groups. In FIG. 3, it is apparent that the reference population has great variation in the IAR, while the galactosemic population has tightly grouped IAR values approaching the IAR of pure Gal-1-P (FIG. 1). A possible explanation is that interfering HMPs contribute to the variability in IAR in the reference population, which have low HMP concentrations. In galactosemia samples, the Gal-1-P fragmentation pattern will dominate for quantitative reasons and the IAR will thus be predicted to approach that of pure Gal-1-P. Use of the IAR makes screening possible without the use of external concentration standards, which simplifies sample preparation and data processing and elites signal variations caused by sample inhomogeneity, as both ion intensities in the IAR will be affected to the same degree A cutoff of 1.5 for the IAR is suggested, which will detect compound heterozygotes and patients with a sensitivity and specificity of 100%. It should be noted, however, that the optimal value of the IAR can differ between screening laboratories depending on the configuration of the tandem MS instrument.

As a byline, galactosemia samples in this study were from patients discovered clinically and diagnosed at an average of 18 (6–36) days of age (table 1). Assuming a reporting delay of two full days from the time of sampling, neonatal screening could have advanced the time of diagnosis in 10/12 patients by an average of 13 days.

Since the method of the invention quantifies total HMP content, not Gal-1-P, it has a potential role in the diagnosis and monitoring of other disorders with affected metabolism of hexose phosphates. And a potential for analytical interference. In addition to other HMPs, detectable analytes could include multiphosphorylated hexoses. For example, biphosphates could interfere, if they yield HMPs by post source decay in mass spectral analysis. Samples could also include other media than blood, as herein before mentioned, e.g. urine or tissue homogenates. Diseases relevant to these considerations include hereditary fructose intolerance (OMIM 229600), fructosuria (hepatic fructokinase deficiency) (OMIM 229800), fructose 1,6-bisphosphatase deficiency (OMIM 229700), glucose-6-phosphate dehydrogenase deficiency (OMIM 305900), and diabetes mellitus.

In a preferred embodiment, the invention provides a novel method of screening for galactosemia. The method uses a minute amount of the samples obtained for routine use by neonatal screening services. Sample preparation is simple. Only common reagents are required. The method quantifies a stable analyte, Gal-1-P. Analysis and interpretation are fully automated, and the diagnostic accuracy is seemingly unsurpassed. As an increasing number of diagnostic facilities have tandem MS to screen for disorders, i.e. in the metabolism of amino acids, organic acids, and fatty acids (10,6), using the tandem MS to also screen for galactosemia would be economical.

Further, the present inventors have made two different extractions of the same dried blood spot with success. The extractions were used to quantitatively analyse two different components. The first extraction was for amino acids and acylcarnitines, which were quantitatively analysed and can be used to screen for related disorders, such as, phenylketournia. The second extraction procedure was for HMPs, as described herein. This second hydrophilic extraction has been proven to give the same result, as if the extraction was carried out on a fresh blood spot.

This method is fast, of the order of 1.5 min per sample (which can be shortened by increasing the flow of the solvent delivery system), economic and easy to apply in a normal routine laboratory with a tandem mass spectrometer.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims. All publications, patents and patent applications are herein incorporated by reference in their entirety to the same extent as if each individual publication, patent or patent application was specifically and individually indicated to be incorporated by reference in its entirety.

TABLE 1

| Birth weight (g) | Age at sampling (days) | Age at diagnosis (days) | Sample age at analysis (years) | HMP conc. (mmol/l) | IAR | Phe (mmol/l) | Tyr (mmol/l) |
|---|---|---|---|---|---|---|---|
| 3810 | 7 | 12 | 15.1 | 3.75 | 1.69 | 303 | 519 |
| 3030 | 5 | 11 | 11.6 | 3.61 | 1.75 | 127 | 362 |
| n/a | 4 | 6 | 9.3 | 3.45 | 1.71 | 306 | 981 |
| 3500 | 5 | 19 | 8.5 | 2.69 | 1.75 | 60 | 69 |
| 2850 | 5 | 27 | 8.3 | 2.66 | 1.75 | 217 | 886 |
| 5300 | 6 | 31 | 5.2 | 2.82 | 1.71 | 114 | 117 |
| 3800 | 4 | 29 | 4.7 | 4.99 | 1.76 | 185 | 345 |
| 3950 | 4 | 15 | 3.8 | 5.15 | 1.73 | 91 | 73 |
| 2850 | 5 | 12 | 3.6 | 2.95 | 1.76 | 301 | 982 |
| 3600 | 4 | 9 | 2.4 | 4.40 | 1.76 | 163 | 765 |
| 3400 | 6 | 7 | 2.2 | 3.05 | 1.72 | 257 | 929 |
| 3088 | 4 | 36 | 0.6 | 5.06 | 1.73 | N/A | N/A |

FULL CITATIONS FOR REFERENCES REFERRED TO IN THE SPECIFICATION

1. Beutler E and Baluda M C. A simple spot screening test for galactosemia. J Lab Clin Med 1966;84:331–335
2. Fujimoto A, Okano Y, Miyagi T, Isshiki G, Oura T. Clin Chem 2000;46:806–10
3. Fujimura Y, Ishii S, Kawamura M, Naruse H. Microdetermination og galactose and galactose-1-phosphate in dried blood spots. Anal Biochem 1981;117:187–95
4. Hill G, O'Reilly D, Robertson E. A simple screening test for galactosemia based on accumulation of galactose and galactose-1-phosphate. In: Naruse H, Irie M (eds.). Proceedings International Symposium on Neonatal Screening for Inborn Errors of Metabolism. Amsterdam: Excerpta Medica 1983;252–3.
5. Komrower G M. Galactosemia—Thirty years on. The experience of a generation. J Inher Metab Dis 1982;5 Suppl 2:96–104
6. Naylor E W, Chace D H. Automated tandem mass spectrometry for mass newborn screening for disorders in fatty acid, organic acid, and amino acid metabolism. J Child Neurol 1999;14 Suppl 1:S4–8
7. Nørgaard-Pedersen B, Simonsen H. Biological specimen banks in neonatal screening. Acta Paediatr Suppl 1999;88 (432): 106–9.
8. Paigen K, Pacholec F, Levy H L. A new method of screening for inherited disorders of galactose metabolism. J Lab Clin Med 1982;99:895–907
9. Pollitt R J, Green A, McCabe I J, Booth A, Cooper N J, Leonard J V et al. Neonatal screening for inborn errors of metabolism: cost, yield and outcome. Health technology assessment 1997;1:49–51
10. Rashed M S, Bucknall M P, Little D, Awad A, Jacob M, Alamoudi M, et al. Screening blood spots for inborn errors of metabolism by electrospray tandem mass spectrometry with a microplate batch process and a computer algorithm for automated flagging of abnormal profiles. Clin Chem 1997;43:71129–1141
11. Schweitzer S. Newborn mass screening for galactosemia. Eur J Pediatr 1995; 154, suppl 2:S37–S39
12. Segal S, Berry G T. In: Scriver C R, Beaudet A L, Sly W S, Valle D. The Metabolic and Molecular Bases of Inherited Disease. 7. ed. 1995;1:967–1000
13. Waggoner D D, Buist N R, Donnel G N. Long-term prognosis in galactosemia: results of a survey of 350 cases. J Inherit Metab Dis 1990;13:802–818
14. Walter J H, Collins J E and Leonard J V. Recommendations for the management of galactosemia. Arch Dis Child 1999;80:93–96
15. Wolucka B A, Rush J S, Waechter C J, Shibaev V N and Hoffmann E. An electrospray-ionization tandem mass spectrometry method for determination of the anomeric configuration of glycosyl 1-phosphate derivatives. Analytical Biochemistry 1998;255:244–251

APPENDIX

MultiView 1.3
File Information for Std. E1
File information:
  Name:        Std. E1
  Type:         Raw Data Format
  Original file:  Std. E1
Log information:
  Vacuum = 2.8 10e−5 torr Occurred on ons 6. okt 1999 at 14:33:35
  Vacuum = 2.8 10e−5 torr Occurred on ons 6. okt 1999 at 14:34:51
Acquisition information:
  Scans in file:      50

APPENDIX-continued

| | |
|---|---|
| Periods in file: | 1 |
| Acquisition date: | onsdag 6. oktober 1999 at 14:33:34 |
| Acquisition duration: | 1 m 15 s |
| Sample name: | Std. E1 |
| Sample ID: | A2 |
| Method path: | Macintosh HD: Screening: Method Gal 1P ugj |

LC method:
  Device Type:    Autosampler
  Device Name:    PE Series 200 Autosampler
  ROM Version:    Series 200 Autosampler, Version Rev 1.05, Serial N
  Comment:    Series 200 Autosampler, Version Rev 1.05, Serial N
  Inject Volume ($\mu$L):    8.0000
  Device specific parameters:    12
  Air Cushion ($\mu$L)    10.0000
  Air Cushion: 0 to 99 $\mu$L.
  Excess Volume ($\mu$L)    5.0000
  Excess Volume: 0 to 100 $\mu$L.
  Sample Speed    0.0000
  Sample Speed: −1 (very slow) to 3 (fast)
  Inject Delay Time (min)    0.0000
  Inject Delay Time in minutes: 0 to 99.99 min.
  Needle Level (%)    20.0000
  Needle Level from the bottom of the vial in: 0 to 100%.
  Flush Volume ($\mu$L)    250.0000
  Flush Volume: 100 to 2500 $\mu$L
  Flush Speed    2.0000
  Flush Speed: 1 (slow) to 3 (fast)
  Pre-Inject Flushes    2.0000
  Number of needle flushes before injection: 0 to 9.
  Post-Inject Flushes    2.0000
  Number of needle flushes after injection: 0 to 9.
  Replicate injections    1.0000
  Number of replicate injections per sample: 1 to 99.
  Analysis Time (min)    0.0000
  The analysis time per injection: 0 to 99.99 minutes.
  Vial Vent Mode    0.0000
  Set the vial vent mode: 0 (no venting) or 1 (venting).

Sample source:
  Autosampler vial:    2
  Component number:    1
  Component name:    Triple Quadrupole LC/MS/MS Mass Spectrometer
  Component ID:    API 300
  Component manufacturer:    Perkin-Elmer Sciex Instruments
  Component serial number:    Pilot 7
  Component software:    Sample Control 1.3
  System version:    Apple ™ Macintosh ® System 8.1
  Application version:    MassChrom 1.0
  Firmware versions:    M401100, B4T0300, M3L1110, B3T0300
  Component model:    P7 030695

Period 1:
  Scans in period:    50
  Relative start time:    2 ms
  MCA count:    0
  Experiments in period:    1
  Cycle Dependent Parameters:    None Period 1. experiment 1:
  Scan type:    MRM
  Polarity:    Negative
  Acquisition mode:    Profile
  Pause time:    2 ms
  Masses requested:

| Q1 Mass (amu) | Q3 Mass (amu) | Dwell Time (ms) |
|---|---|---|
| 259.02 | 78.96 | 500 |
| 259.02 | 96.97 | 500 |
| 259.02 | 138.98 | 500 |

State file: Macintosh HD:Screening:statefiles::gal 1p msms SSI
State table parameters:

| Parm. | Value |
|---|---|
| IS | −4900 |
| NC | 0 |
| TEM | 0 |
| OR | −20 |
| RNG | −140 |
| Q0 | 8.800 |
| IQ1 | 11 |
| ST | 10.799 |
| RO1 | 10.999 |
| IQ2 | 19.999 |

APPENDIX-continued

```
RO2    33
IQ3    50
RO3    38
DF     399.003
CEM    2400
NEB    15
CUR    12
CAD    2
QPE    0
POL    1
VCM    0
IPE    0
```
Peak width resolution:
Q1 peak widths:

| Mass: | Offset: |
|---|---|
| 30 | −0.020 |
| 100 | 0.018 |
| 1000 | 0.125 |
| 2000 | 0.245 |
| 3000 | 0.355 |

Q3 peak widths:

| Mass: | Offset: |
|---|---|
| 30 | 0.030 |
| 100 | 0.040 |
| 1000 | 0.160 |
| 2000 | 0.330 |
| 3000 | 0.470 |

Calibration files:
Q1 calibration file:   Macintosh HD:API FOLDER:CALIB. FILER::Gal 1p Q1 cal.
Q3 calibration file:   Macintosh HD:API FOLDER:CALIB. FILER::Gal 1p Q3 cal.
Calibration tables:
Q1 calibration:

| Mass: | DAC value: |
|---|---|
| 59.060 | 1102 |
| 175.130 | 3321 |
| 259.138 | 4930 |
| 616.464 | 11766 |
| 906.673 | 17319 |
| 1254.925 | 23983 |
| 1545.134 | 29537 |
| 2010.469 | 38444 |
| 2242.637 | 42890 |

Q3 calibration:

| Mass: | DAC value: |
|---|---|
| 78.96 | 1485 |
| 96.97 | 1830 |
| 138.98 | 2634 |

What is claimed is:

1. A method for detecting and quantitatively analysing hexosemonophosphates in a biological sample comprising:
   (a) obtaining an extract of the biological sample in a form suitable for ionization;
   (b) ionizing the extract to form a stream of gas phase ions;
   (c) selecting precursor molecular ions having a mass to charge ratio of hexosemonophosphate;
   (d) fragmenting the precursor molecular ions to obtain product ions of hexosemonophosphate;
   (e) selecting product ions of interest from other product ions by their mass to charge ratio;
   (f) detecting the product ions of interest and obtaining their ion intensities;
   (g) using the ion intensities of the product ions to:
      (i) determine by spectrum analysis the quantitative abundance of hexosemonophosphates in the biological sample; and/or
      (ii) determine the concentration of hexose- monophosphates or a particular species thereof by comparing the ion intensities of a control sample or samples having a known concentration of hexose-monophosphates and/or the particular species thereof; and/or
      (iii) determine ion abundance ratios (IAR) indicating the relative amount of a hexose-monophosphate species present within the biological sample.

2. The method of claim 1 wherein the hexose-monophosphate extract of the biological sample, suitable for ionization is obtained by obtaining a biological sample to be analysed, drying the biological sample and extracting the dried sample with a solvent suitable for extracting hexose monophosphates from the sample.

3. The method of claim 2 wherein the biological sample is blotted onto a suitable medium and then dried.

4. The method of claim 3 wherein the suitable medium is filter paper.

5. The method of claim 2 wherein the solvent suitable for extracting hexosemonophosphates is a solvent that is more hydrophilic than methanol.

6. The method of claim 5 wherein the solvent is selected from the group consisting of: acetonitrile in water, ethyl acetate in water, tetrahydrofuran in water, methanol in water, and isopropanol in water or a solvent with characteristics similar thereto.

7. The method of claim 6 wherein the solvent is 30:70 to 70:30 (v/v) acetonitrile in water.

8. The method of claim 7 wherein the solvent is 1:1 (v/v) acetonitrile in water.

9. The method of claim 1 wherein the biological sample is selected from the group consisting of: whole blood, fractionated blood components, tissue, urine, stool, bile, saliva, sweat or other glandular secretions.

10. The method of claim 9 wherein the biological sample is a whole blood sample.

11. The method of claim 10 wherein the blood sample is blotted onto a suitable medium, dried and then extracted using a solvent suitable for extracting hexosemonophosphates.

12. The method of claim 11, wherein the suitable medium is filter paper.

13. The method of claim 1 wherein the steps (b) to (e) are preformed in a tandem mass spectrometer.

14. The method of claim 13, wherein the ion intensities are recorded in negative-ion mode.

15. The method of claim 1 wherein step (b) comprises forming the stream of ions by electrospray or pneumatically assisted electrospray ionization.

16. The method of claim 1 wherein the mass to charge ratio of the precursor molecular ions of HMP is 259.02 Da/e.

17. The method of claim 1 wherein the product ions of interest are: $[PO_3]^-$, $[H_2PO_4]^-$, and $[(C_2H_3O)HPO_4]^-$.

18. The method of claim 17 wherein the mass-to-charge ratio of the productions of interest are: 78.96 Da/e for $[PO_3]^-$, 96.97 Da/e for $[H_2PO_4]^-$; and 138.98 for $[(C_2H_3O)HPO_4]^-$.

19. The method of claim 18, wherein the $[PO_3]^-$ product ion is most indicative of aldose hexose-1-monophosphates and wherein the $[H_2PO_4]^-$ product ion is most indicative of either aldose hexose-6-monophosphates or ketose hexose-1-or 6-monophosphates.

20. The method of claim 19 wherein Gal-1-P is an aldose hexose-1-monophosphate and the ion intensity of the $[PO_3]^-$ fragment is used to determine the concentration of hexose-monophosphates indicative of that of Gal-1-P in the biological by comparing the ion intensities of the $[PO_3]^-$ fragment in the biological sample with that of a control sample with a known concentration of Gal-1-P.

21. The method of claim 18 wherein the ion abundance ratio of the product ions 78.96 Da/e to 96.97 Da/e is used as an indicator of Gal-1-P concentration in the biological sample.

22. A method of screening for and/or diagnosing galactosemia by comparing the hexose-monophosphate concentration and/or IAR level in a biological sample of a test patient as determined by claim 20 or 21 with that of a cutoff level indicative of galactosemia.

23. The method of claim 12 wherein the cutoff level of hexosemonophosphate is between 0.95–2.6 mmol/l of HMP concentration and/or 1.41–1.68 IAR, wherein levels above the cutoff are indicative of galactosemia.

24. The method of claim 23 wherein the cutoff level is 1.2 mmol/l hexosemonophosphate concentration and/or 1.5 IAR.

25. The method of claim 12, wherein the biological sample is a whole blood sample extracted with a solvent suitable for extracting hexose-monophosphates.

26. The method of claim 25 wherein the solvent is 30:70 to 70:30 v/v acetonitrile in the water.

27. A method for diagnosing a hexose-monophosphate disorder in an individual by determining the hexose-monophosphate level in the patient using the method of claim 1 and comparing it with the hexose-monophosphate cutoff level indicative of the disorder.

28. The method of claim 27, wherein the hexose-monophosphate disorder is selected from the group consisting of: galactosemia (OMIM 230400), hereditary fructose intolerance (OMIM 229600), fructosuria (hepatic fructokinase deficiency) (OMIM 229800), Fructose 1,6-bisphosphatase deficiency (OMIM 229700), glucose-6-phosphate dehydrogenase deficiency (OMIM 305900), and diabetes mellitus.

29. The method of claim 3 wherein before the biological sample is extracted with a solvent suitable for extracting hexose monophosphates, amino acids and acylcarnitines are extracted from the dried biological sample using a suitable solvent forming an initial extract which is removed for quantitative analysis, the original biological sample is then redried.

30. The method of claim 29 wherein the biological sample is whole blood.

31. The method of claim 29, wherein the suitable solvent is methanol.

32. The method of claim 29 for screening for both metabolic disorders of amino acids, organic acids, and fatty acids and for metabolic disorders of hexosemonophosphates.

33. The method of claim 32 for screening for both phenylketournia and galactosemia.

34. The method of claim 1 wherein the product ion of interest is $[PO_3]^-$.

35. The method of claim 34 wherein the ion intensity of $[PO_3]^-$ is used to determine the concentration or level of aldose-hexose-1-monophosphates in the biological sample.

36. The method of claim 35 to diagnose an aldose hexose-1-monophosphate related disorder wherein the aldose-hexose-1-monophosphate concentration or level is compared to a cut off concentration or level of aldose-hexose-1-monophosphate that is indicative of the disorder.

37. The method of claim 36 wherein the disorder is galactosemia.

38. The method of claim 37 wherein the cutoff level of hexose-1-monophosphate is between 0.95–2.6 mmol/l of hexose 1-monophosphate concentration and/or 1.41–1.68 IAR, wherein levels above the cutoff are indicative of galactosemia.

39. The method of claim 38 wherein the cutoff level is 1.2 mmol/l hexose-1-monophosphate concentration and/or 1.5 IAR.

40. The method of claim 1 wherein the product ion of interest is $[H_2PO_4]^-$.

41. The method of claim 40 wherein the ion intensity of $[H_2PO_4]^-$ is used to determine the concentration or level of aldose hexose-6-monophosphates, and/or ketose hexose-1-monophosphates and/or ketose hexose-6-monophosphates in the biological sample.

* * * * *